US012653230B2

(12) United States Patent
Webski

(10) Patent No.: US 12,653,230 B2
(45) Date of Patent: Jun. 16, 2026

(54) CUSTOMIZABLE PORTABLE VAPORIZER

(71) Applicant: SWEETSPOT BRANDS LLC, Portsmouth, RI (US)

(72) Inventor: Jason Webski, Stamford, CT (US)

(73) Assignee: SWEETSPOT BRANDS LLC, Portsmouth, RI (US)

( * ) Notice: Subject to any disclaimer, the term of this patent is extended or adjusted under 35 U.S.C. 154(b) by 0 days.

(21) Appl. No.: 18/642,199

(22) Filed: Apr. 22, 2024

(65) Prior Publication Data

US 2024/0268458 A1     Aug. 15, 2024

Related U.S. Application Data

(63) Continuation of application No. 16/988,714, filed on Aug. 9, 2020, now Pat. No. 11,992,042.

(60) Provisional application No. 62/884,373, filed on Aug. 8, 2019.

(51) Int. Cl.
| | |
|---|---|
| *A24F 40/30* | (2020.01) |
| *A24B 15/167* | (2020.01) |
| *A24F 40/10* | (2020.01) |
| *A24F 40/42* | (2020.01) |
| *A24F 40/44* | (2020.01) |
| *A24F 40/46* | (2020.01) |
| *A24F 40/485* | (2020.01) |
| *A61K 31/00* | (2006.01) |
| *A61M 11/04* | (2006.01) |
| *A61M 15/00* | (2006.01) |

(52) U.S. Cl.
CPC ............ *A24F 40/30* (2020.01); *A24B 15/167* (2016.11); *A24F 40/10* (2020.01); *A24F 40/42* (2020.01); *A24F 40/44* (2020.01); *A24F 40/46* (2020.01); *A24F 40/485* (2020.01); *A61K*

31/658 (2023.05); *A61M 11/042* (2014.02); *A61M 15/0021* (2014.02); *A61M 2205/8206* (2013.01)

(58) Field of Classification Search
CPC .......... A24F 40/10; A24F 40/30; A24F 40/42; A24F 40/44; A24F 40/46; A24F 40/485
See application file for complete search history.

(56) References Cited

U.S. PATENT DOCUMENTS

| | | | | |
|---|---|---|---|---|
| 10,104,914 B2 * | 10/2018 | Force | | A24F 40/42 |
| 10,244,792 B2 * | 4/2019 | Rado | | H05B 3/46 |
| 10,433,585 B2 * | 10/2019 | Tucker | | A24F 40/30 |
| 10,925,317 B2 * | 2/2021 | Smith | | A24F 40/30 |
| 11,147,313 B2 * | 10/2021 | Rado | | A24F 40/48 |
| 11,344,066 B2 * | 5/2022 | Rado | | A24F 40/10 |

(Continued)

FOREIGN PATENT DOCUMENTS

| | | | | |
|---|---|---|---|---|
| WO | WO-2020070513 A1 * | 4/2020 | | A24F 40/10 |

*Primary Examiner* — Abdullah A Riyami
*Assistant Examiner* — Thang H Nguyen
(74) *Attorney, Agent, or Firm* — Kelley Drye & Warren LLP

(57) ABSTRACT

A portable vaporizer for the delivery of inhalable substances is presented that has the capability of combining multiple different cartridges to provide the user with a variety of inhalable substances for inhalation. Each cartridge may comprise a heating element, a chimney contact connector located at a first end of the cartridge, a distal contact connector located at a second end of the cartridge, and one or more electrical connections between the heating element, the chimney contact connector, and the distal contact connector.

20 Claims, 16 Drawing Sheets

Figure 4B

(56)         References Cited

U.S. PATENT DOCUMENTS

| | | | | |
|---|---|---|---|---|
| 11,825,883 | B2* | 11/2023 | Rado .................... | H05B 1/0244 |
| 2015/0313275 | A1* | 11/2015 | Anderson ............. | A24B 15/10 |
| | | | | 131/352 |
| 2016/0219938 | A1* | 8/2016 | Mamoun ................ | G05B 15/02 |
| 2018/0177233 | A1* | 6/2018 | Tucker ................... | A24F 40/40 |
| 2018/0325176 | A1* | 11/2018 | Burseg .................. | A24F 40/30 |
| 2020/0015524 | A1* | 1/2020 | Rado ....................... | A24F 40/46 |
| 2021/0204594 | A1* | 7/2021 | Rees ....................... | A24D 1/20 |
| 2021/0219609 | A1* | 7/2021 | Rado ....................... | A24F 40/10 |
| 2022/0167668 | A1* | 6/2022 | Paton .................. | A24B 15/167 |
| 2023/0076259 | A1* | 3/2023 | Pettitt .................. | A24F 40/485 |
| 2023/0172283 | A1* | 6/2023 | Kwon ...................... | A24F 7/00 |
| | | | | 131/328 |

* cited by examiner

CUSTOMIZABLE PORTABLE VAPORIZER

CROSS REFERENCE TO RELATED APPLICATIONS

This application is a continuation application of U.S. patent application Ser. No. 16/988,714, filed Aug. 9, 2020 and now U.S. Pat. No. 11,992,042, issued May 28, 2024, which claims the benefit of U.S. Provisional Patent Application No. 62/884,373, filed Aug. 8, 2019. The entire contents of these applications are incorporated herein by reference in their entirety.

FIELD OF INVENTION

The present invention relates to portable vapor delivery systems for the delivery of inhalable substances. More specifically the present invention relates to vapor delivery systems with the capability to incorporate one or more cartridges with a variety of inhalable substances for inhalation.

BACKGROUND OF THE INVENTION

Many plant materials contain active ingredients that, when inhaled in vapor form, provide an effect to the user. Traditionally, a user would create a vapor of the active ingredients from such plants by burning the plant and inhaling the resulting fumes. Those fumes, however, typically include not only the beneficial vapors from the active ingredient, but also vapors and smoke produced from burning the inactive parts of the plant as well, which may be toxic.

Electronic cigarettes and portable vaporizers known in the art may be used to vaporize tobacco, cannabinoids, and other products to generate a vapor that can be inhaled. An example of a portable vaporizer is disclosed in U.S. Pat. No. 10,244,792. The active ingredient from a plant material, such as example nicotine or *cannabis*, can be extracted, purified, and converted into a vaporizing liquid. The vaporizing liquid (including the active ingredient) can then be vaporized in an electronic cigarette or portable vaporizer absent the potentially harmful byproducts included in the remaining organic material in the plant material.

Not all of the inactive ingredients in plants are harmful when burned, however. Terpenes are aromatic oils produced by plants and provide distinctive aromas. They may be used in aromatherapy, traditional medicines, and perfumes. Terpenes may also be found in plants smoked for their active ingredients. In *cannabis*, for example, the same glands that produce cannabinoid oils also produce terpenes. These *cannabis* terpenes are the aromatic oils that provide *cannabis* varietals with their distinctive smells.

When cannabinoids, such as isomers of tetrahydrocannabinol ("THC") and cannabidiol ("CBD"), are extracted from *cannabis*, standard extraction processes separate the target cannabinoid oil from *cannabis* terpenes. Thus, a vaporizer that creates vapor from a cannabinoid oil without terpenes will be devoid of the aroma and flavors associated with *cannabis*.

Vaporizing terpenes originally present with the cannabinoid oil may allow a user to experience aromas and flavors associated with those terpenes. Inhaling terpenes and other aromas associated with *cannabis* may also have independent health benefits and/or enhance the "high" experience from inhaling cannabinoid vapors. To re-introduce the familiar aromas of *cannabis* with the cannabinoid oil, current cannabinoid oil cartridges may recombine the cannabinoid oil with terpenes for flavor and effect, prior to packaging for consumers. Consumers are therefore presented with a limited variety of flavors/terpene combinations. Further, once purchased, users are bound to the single flavor option purchased.

Accordingly, there is a need for a vaporizer that allows flavors/terpenes and/or combinations thereof to be used interchangeably with one or more active ingredients, such as cannabinoid oil or nicotine. Allowing users to not only try different terpene combinations, but also interchange terpene combinations throughout the life of the vaporizer, will allow users to customize their vaporization experience.

SUMMARY OF THE INVENTION

An exemplary embodiment of the present invention is a portable vaporizer that includes a primary cartridge into which a first vaporizing liquid may be inserted, and one or more secondary cartridges into which additional vaporizing liquids may be inserted. For example, a portable vaporizer in accordance with the present invention may include a primary cartridge that may be used to hold and vaporize a first vaporizing liquid containing unflavored or mildly flavored THC, and a secondary cartridge that may be used to hold and vaporize terpenes and/or one or more flavors. The present invention may thereby allow a user to customize and change the flavor of the vapors generated by the portable vaporizer. It may also allow the user to try different terpene combinations and enhance their experience throughout the life of a single primary cartridge.

The vaporizable material inserted in the primary and/or secondary cartridges may comprise, for example, nicotine solutions (e.g., nicotine salt in an aqueous solution), a *cannabis* liquid (e.g., a viscous *cannabis*-containing material), or any other pharmaceutical material. The vaporizable material may contain a medicinal compound as an active ingredient. Preferably, medicinal compounds inserted in the primary or secondary cartridge(s) of the present invention may be heated without combustion to vaporization for inhalation delivery at a temperature range of, e.g., about 100° C. (e.g., for water-based carriers, e.g., about 100° C., 105° C., 110° C., 120° C., 130° C., 140° C., 150° C., 160° C., 170° C., etc.; for ethanol-based formulations, e.g., about 50° C., about 60° C., about 70° C., about 80° C., etc.) to about (e.g., below) the temperature at which the active ingredient thermally decomposes (e.g., less than about 150° C., 160° C., 170° C., 180° C., 190° C., 200° C., 210° C., 220° C., 230° C., 240° C., 250° C., 260° C., 270° C., 280° C.; 290° C., 300° C., etc.).

Drugs inserted in the primary cartridge and/or secondary cartridges may be neat or solubilized in a pharmaceutically acceptable solvent. The drugs can include over the counter (OTC) substances used as aides for various ailments including known respiratory aides for asthma or chronic obstructive pulmonary disease (COPD), analgesics and internal medication aides (e.g., ibuprofen, naproxen), heartburn aides (e.g., omeprazole), sleeping aides (e.g., doxylamine, diphenhydramine, melatonin), and/or motion sickness aides (e.g., meclizine). The vaporizable material may contain short acting beta-agonist (e.g., albuterol, levalbuterol, pirbuterol), long acting beta-agonist (e.g., salmeterol, formoterol), anti-cholinergics (e.g., atropine sulfate, ipratropium bromide), leukotriene modifiers (e.g., montelukast, zafirlukast), cartico-steriods (e.g., fluticasone, budesonide, mometasone), theophylline (e.g., theophylline), or combination corticosteroid and beta agonist. The vaporizable material can contain botanicals and/or nutraceuticals such as tea (polyphenols, flavonoids, green tea catechins); horehound (phenol flavonoid glycosides, labdane diterpenoids, yohimbe, cranberry/grape (proanthocyanidins), black cohosh (terpene glycoside fraction (actine/cimifugoside), flax seed (omega fatty acids), *echinacea* (echinacoside), valerian (alkaloids, gabapentin, isovaleric acid, terpenes), *senna* (*senna* cglycosides), cinnamon (cinnamaldehyde, phenols, terpenes), vitamin D, saw palmetto (fatty acids), or caffeine. In certain embodiments, the vaporizable material may be soluble to at least fifty percent by weight in any suitable carrier solvent such as glycols (such as propylene glycol and vegetable glycerin), ethylene glycol, dipropylene glycol, trimethylene glycol, ethanol, and combinations thereof. The medicinal compound may be terpinolene, THC, nicotine, Linalool, phytol, beta myrcene, citronellol, caryophyllene oxide, alpha pinene, limonene, beta caryophyllene, humulene. The vaporizable material may be, for example, an essential oil or a terpene from the *cannabis* plant.

BRIEF DESCRIPTION OF DRAWINGS

A further understanding of the invention can be obtained by reference to exemplary embodiments set forth in the illustrations of the accompanying drawings. Although the illustrated embodiments are merely exemplary of systems, methods, and apparatuses for carrying out the invention, both the organization and method of operation of the invention, in general, together with further objectives and advantages thereof, may be more easily understood by reference to the drawings and the following description. Like reference numbers generally refer to like features (e.g., functionally similar and/or structurally similar elements).

The drawings are not necessarily depicted to scale; in some instances, various aspects of the subject matter disclosed herein may be shown exaggerated or enlarged in the drawings to facilitate an understanding of different features. Also, the drawings are not intended to limit the scope of this invention, which is set forth with particularity in the claims as appended hereto or as subsequently amended, but merely to clarify and exemplify the invention.

FIG. 8 depicts a bottom chamber gasket in accordance with the present invention.

FIG. 12 depicts a top chamber gasket in accordance with the present invention.

DETAILED DESCRIPTION

The invention may be understood more readily by reference to the following detailed descriptions of embodiments of the invention. However, techniques, systems, and operating structures in accordance with the invention may be embodied in a wide variety of forms and modes, some of which may be quite different from those in the disclosed embodiments. Also, the features and elements disclosed herein may be combined to form various combinations without exclusivity, unless expressly stated otherwise. Consequently, the specific structural and functional details disclosed herein are merely representative. Yet, in that regard, they are deemed to afford the best embodiments for purposes of disclosure and to provide a basis for the claims herein, which define the scope of the invention. It must be noted that, as used in the specification and the appended claims, the singular forms "a", "an", and "the" include plural referents unless the context clearly indicates otherwise.

Use of the term "exemplary" means illustrative or by way of example, and any reference herein to "the invention" is not intended to restrict or limit the invention to the exact features or steps of any one or more of the exemplary embodiments disclosed in the present specification. Also, repeated use of the phrase "in one embodiment," "in an exemplary embodiment," or similar phrases do not necessarily refer to the same embodiment, although they may. It is also noted that terms like "preferably," "commonly," and "typically," are not used herein to limit the scope of the claimed invention or to imply that certain features are critical, essential, or even important to the structure or function of the claimed invention. Rather, those terms are merely intended to highlight alternative or additional features that may or may not be used in a particular embodiment of the present invention.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Figure 1:
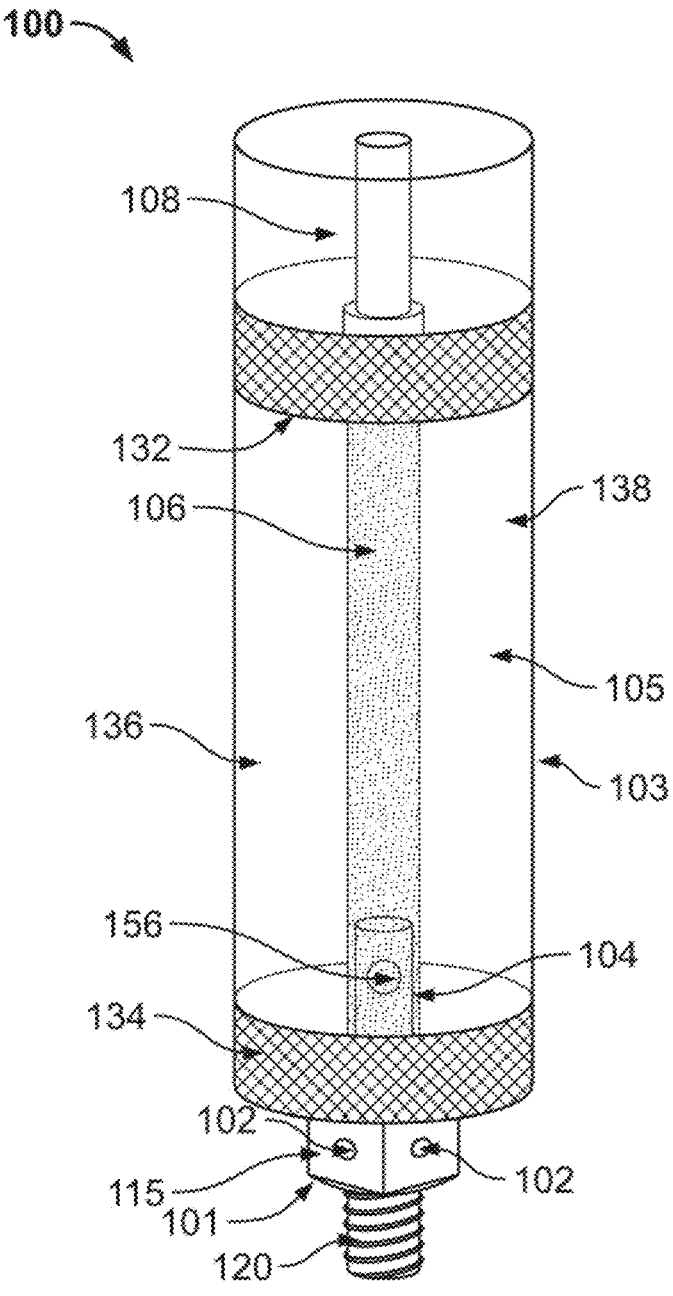
FIG. 1 is a perspective view of a vaporizer in accordance with the present invention.

FIG. 1 depicts a first exemplary embodiment of a portable vaporizer (100). Portable vaporizer (100) includes primary cartridge (103) having an outer housing (105) extending along a first longitudinal axis from a first end (132) to a second end (134). Outer housing (105) may include one or more walls (138) extending from first end (132) to second end (134) and enclosing an internal space (136) between first end (132) and second end (134). First end (132) of outer housing (105) may be capable of connecting to a mouthpiece (108).

An internal chimney (106) within one or more walls (138) of outer housing (105) may extend along the first longitudinal axis from the first end (132) to the second end (134) of outer housing (105). Internal chimney (106) may be centered within internal space (136), or may be offset. Internal chimney (106) is preferably a hollow cylinder having a circular cross section, but internal chimney (106) may have a cross section of any shape, such as a hollow square or octagon. A filter (104) may be located within internal chimney (106). Filter (104) may fill the entire internal cavity of internal chimney (106) or may fill part of the internal cavity of internal chimney (106). As shown in FIG. 1, filter (104) may be located at one end of internal chimney (106), such as the end of internal chimney (106) closest to the second end (134) of outer housing (105).

Second end (134) of outer housing (105) may include a power source connection (101) capable of connecting to a power source such as a battery. The power source connection (101) may have a base portion (115) and a threaded portion (120). Base portion (115) may include one or more apertures (102). The power source may include a rechargeable battery, such as a lithium-ion battery, enclosed within a battery casing (not shown). The battery may include a threaded bore capable of mating with threaded portion (120) of power source connection (101). Alternatively, the battery may be connected to the primary cartridge in any number of ways, including with a snap fit, a bayonet connection, or a press fit.

A battery contact may be disposed within the threaded bore. An electronic controller may also be included within the battery casing to control voltage, current, and/or timing. A button may be provided for selectively actuating electricity delivery from the battery to the primary cartridge (103). In some embodiments, the button can include a light that indicates when power may be being delivered.

At the second end (134) of outer housing (105) may be a compartment (not shown) that contains a heating element (i.e., atomizer). The heating element may be a metal coil. Power source connection (101) may be electrically connected to the heating element. Apertures (102) may be in fluid communication with the compartment, and the compartment may be in fluid communication with the internal cavity of internal chimney (106).

The portion of internal space (136) between the internal chimney (106) and one or more walls (138) may also be in fluid communication with the compartment. Vaporizing material in internal space (136) may pass to the compartment and contact the heating element. For example, aperture (156) in internal chimney (106) may allow the vaporizing material to pass into the compartment. Filter (104) may be placed in internal chimney (106) so as to fully or partially block aperture (156).

When electricity is provided from a power source to the power source connector (101), the electricity may be delivered to the heating element, generating heat and vaporizing the vaporizing material from the primary cartridge (103), creating vapors. When a user inhales from mouthpiece (108), air may be drawn through apertures (102), through the compartment in the second end (134) of outer housing (105), mixing with the vapors. The air and vapor mixture may then be drawn through filter (104) and internal chimney (106), and through mouthpiece (108), to the user's mouth.

Figure 2:
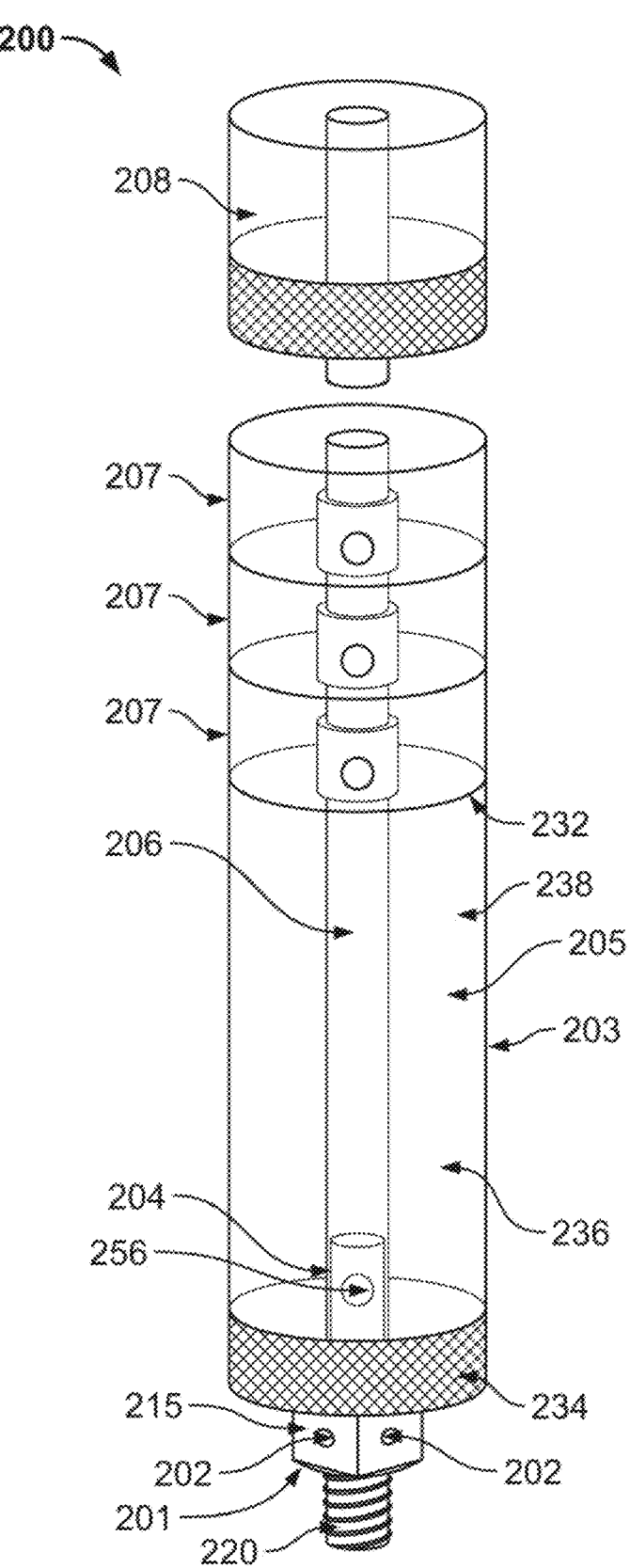
FIG. 2 is a perspective view of a vaporizer in accordance with the present invention.

FIG. 2 depicts a second exemplary embodiment of a portable vaporizer (200). Portable vaporizer includes the same elements as portable vaporizer (100) depicted above in FIG. 1, including primary cartridge (203) having outer housing (205) extending along a first longitudinal axis from a first end (232) to a second end (234). Outer housing (205) may include one or more walls (238) extending from first end (232) to second end (234) and enclosing an internal space (236) between first end (232) and second end (234). First end (232) of outer housing (205) may be capable of connecting to a mouthpiece (208).

An internal chimney (206) within one or more walls (238) of outer housing (205) may extend along the first longitudinal axis from the first end (232) to the second end (234) of outer housing (205). Internal chimney (206) may be centered within internal space (236), or may be offset. Internal chimney (206) is preferably a hollow cylinder having a circular cross section, but internal chimney (206) may have a cross section of any shape, such as a hollow square or octagon. A filter (204) may be located within internal chimney (206). Filter (204) may fill the entire internal cavity of internal chimney (206) or may fill part of the internal cavity of internal chimney (206). As shown in FIG. 2, filter (204) may be located at one end of internal chimney (206), such as the end of internal chimney (206) closest to the second end of outer housing (205).

Second end (234) of outer housing (205) may include a power source connection (201) capable of connecting to a power source such as a battery. As described above for portable vaporizer (100), the power source connection (201) may have a base portion (215) and a threaded portion (220). The base portion (215) may include one or more apertures (202). At second end (234) of outer housing (205) may be a compartment (not shown) that contains a heating element (i.e. atomizer). The heating element may be a metal coil. Power source connection (201) may be electrically connected to the heating element. The apertures (202) in the base portion (215) may be in fluid communication with the compartment, and the compartment may be in fluid communication with the internal cavity of internal chimney (206). When electricity is provided from a power source to the power source connector, the electricity may be delivered to the heating element, generating heat and vaporizing liquid in primary cartridge (203), creating vapors.

One or more secondary cartridges (207) may be attached to the first end (232) of primary cartridge (203). Secondary cartridges (207) may be removably attached to primary cartridge (203) or may be fixedly attached.

When a user inhales from mouthpiece (208), air may be drawn through apertures (202), through the compartment in the second end (234) of outer housing (205), mixing with the vapors. The air and vapor mixture may then be drawn through filter (204) and internal chimney (206), through any secondary cartridges (207) attached to the first end (232) of primary cartridge (203), and through mouthpiece (208), to the user's mouth. The space between the internal chimney (206) and one or more walls (238) may be filled with one or more flavors and/or terpenes. An aperture (256) in internal chimney (106) may allow the one or more flavors and/or terpenes to pass into internal chimney (206) when a user inhales through mouthpiece (208), thereby causing the one or more flavors and/or terpenes to mix with the air and vapor mixture. Filter (204) may be placed in internal chimney (206) so as to fully or partially block aperture (256). However, filter (204) may allow the one or more flavors and/or terpenes to pass into internal chimney (206) when a user inhales through mouthpiece (208).

Figure 3:
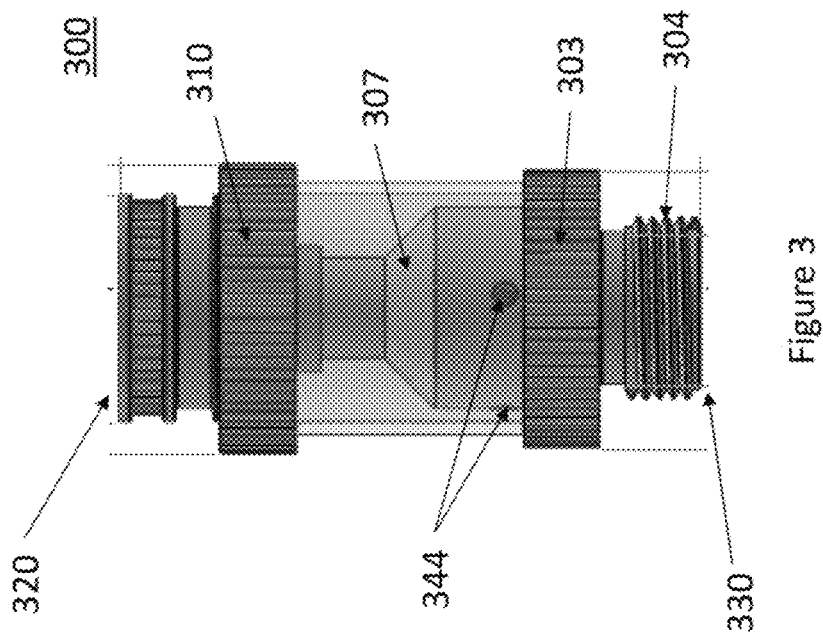
FIG. 3 depicts a cartridge in accordance with the present invention.
Figures 4A, 4B:
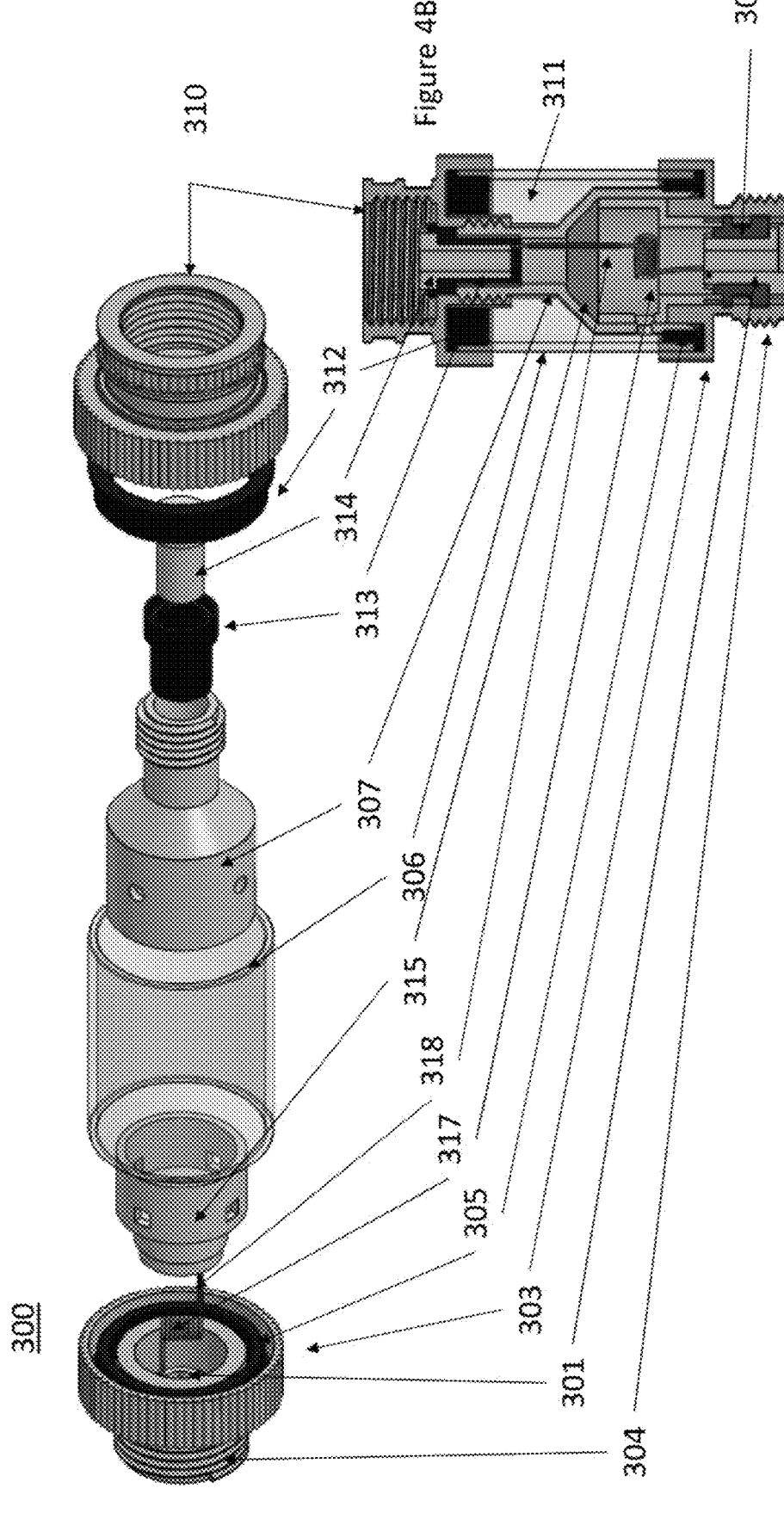
FIG. 4A is an exploded view of the cartridge depicted in FIG. 3.
FIG. 4B is a cross-sectional view of the cartridge depicted in FIG. 3.

FIG. 3 depicts an exemplary cartridge (300) in accordance with the present invention that may serve as either a primary cartridge (203) or secondary cartridge (207). FIG. 4A depicts and exploded view of cartridge (300) and FIG. 4B depicts a cross sectional view of cartridge (300). Cartridge (300) extends from a first end (320) to a second end (330). At first end (320) is top adapter (310). At second end (330) is distal base (303). Extending between top adaptor (310) and distal base (303) is a chamber (306). Within chamber (306), also extending from top adaptor (310) to distal base (303) is chimney (307).

Figures 7A, 7B:
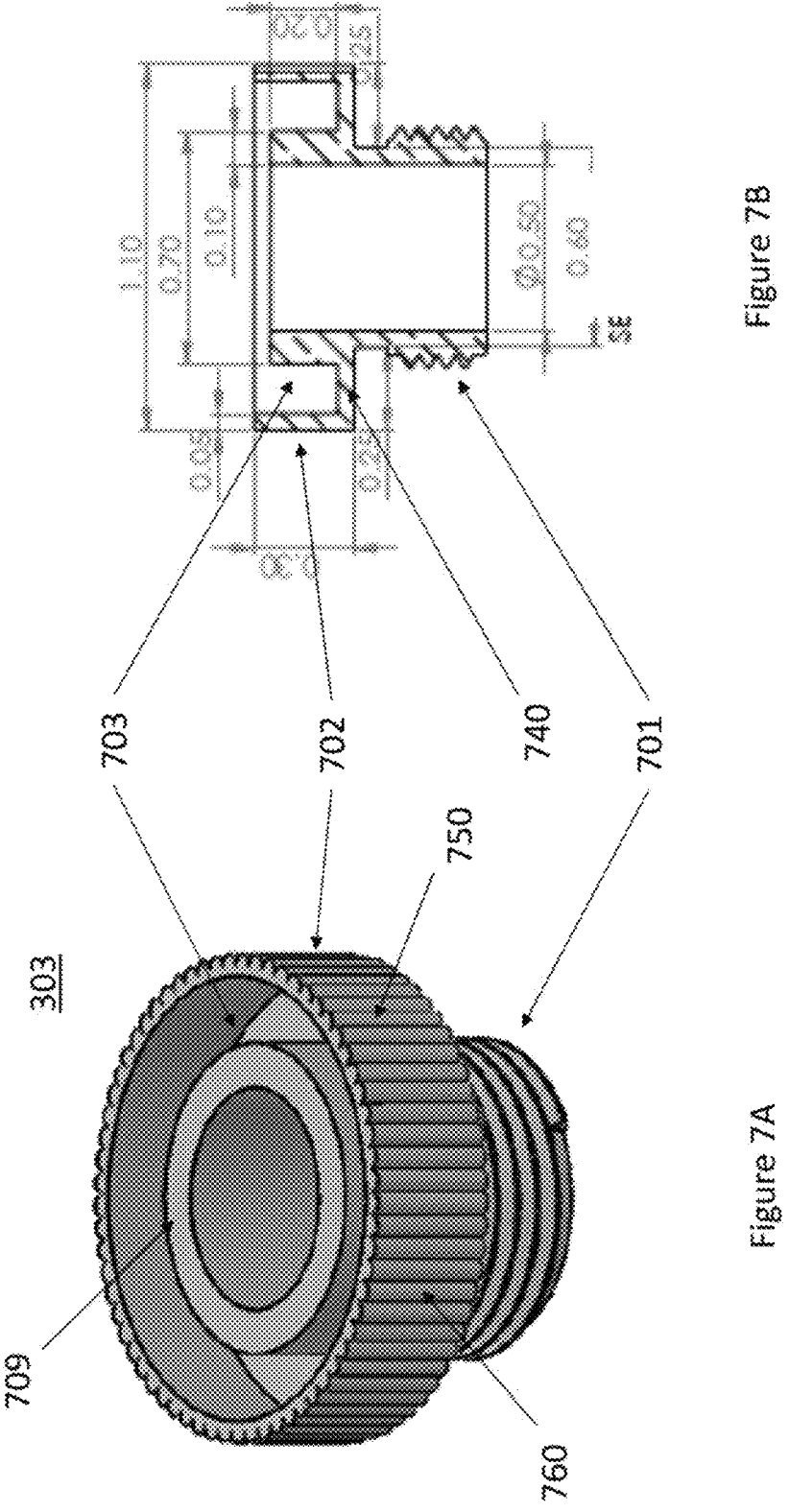
FIGS. 7A and 7B depict a distal base in accordance with the present invention.

Referring also to FIGS. 7A and 7B, distal base (303) may be generally cylindrical in shape and may have three sections: (1) an inner tubular distal base cylinder (701); (2) a distal base mount boss (702); and (3) a cylindrical portion (709) extending above the inner tubular distal base cylinder (701). The external surface of the inner tubular distal base cylinder (701) may include threads (304).

The inner tubular distal base cylinder (701) may have an internal diameter that may be sufficient to include both the distal contact (301) and the distal contact gasket (302) preferably 0.5 cm. This may allow the cartridge (300) to be screwed into the power source (201) if the cartridge (300) may be serving as the primary cartridge (203). Alternatively, the distal threads (304) may be used to screw the distal base (303) to a top adapter (310) of another cartridge (300) if the cartridge may be serving as a secondary cartridge (207).

The distal base mount boss (702) may comprise a flange (740) and a cylindrical wall (750) having a wider diameter than the inner tubular distal portion-preferably 1.1 cm. The exterior of cylindrical wall (750) may include ridges (760) to provide assistance in screwing the cartridge (300).

Distal base mount boss (702) and cylindrical portion (709) may form a distal base ring cavity (703). The distal base (303) may be made of any material, including metals such as aluminum, brass, steel, and stainless steel.

Figures 11A, 11B:
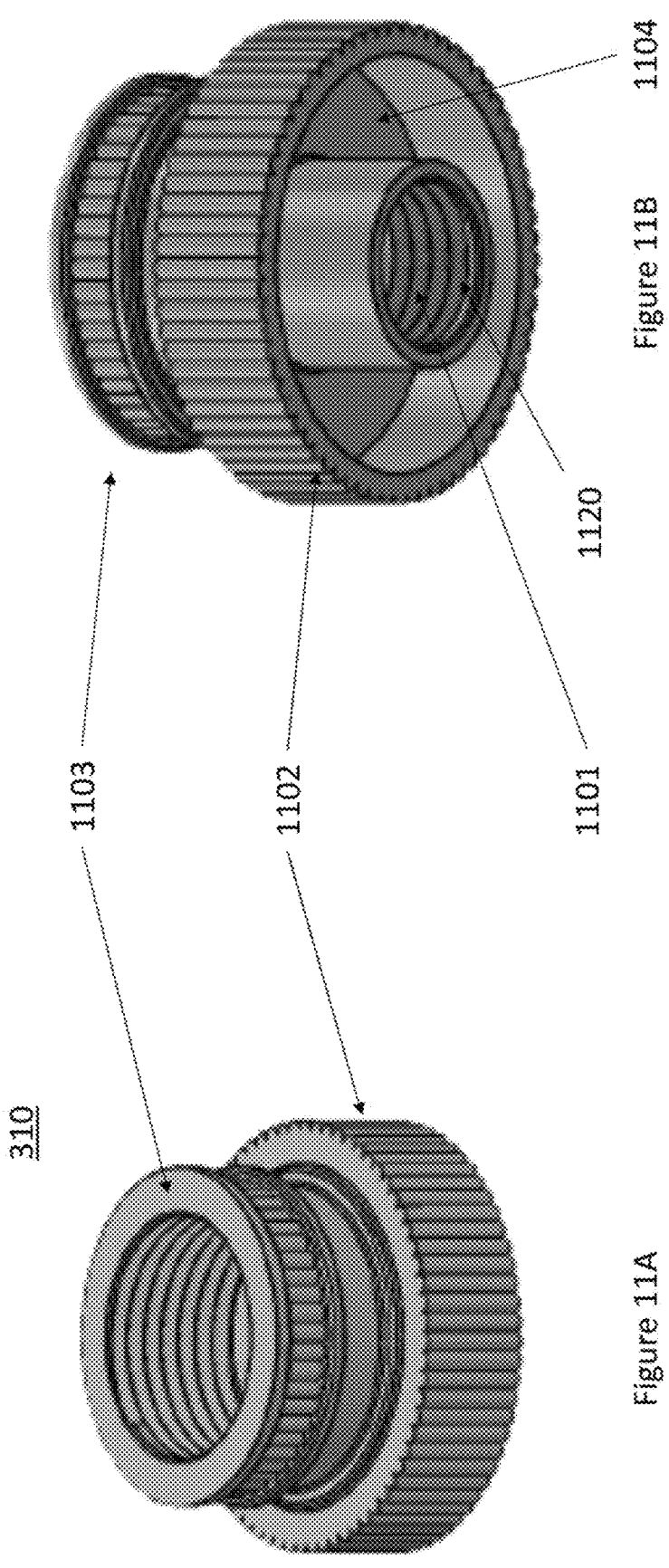
FIGS. 11A and 11B depict a top adapter in accordance with the present invention.

Referring to FIGS. 11A and 11B, top adapter (310) may be generally cylindrical in shape with three sections: (1) a distal tubular cylinder (1101), (2) a top adapter mounting flange (1102) extending radially from the distal internally threaded tubular cylinder (1101), and (3) a proximal internally threaded tubular cylinder (1103) having a diameter and a length. Top adaptor (310) may be, for example, a 510 Adapter known in the art. The internal surface of distal tubular cylinder (1101) may have threads (1120). The external surface of a distal tubular cylinder (1101) and top adapter mounting flange (1102) may form a top adapter mounting cavity (1104).

Figure 9:
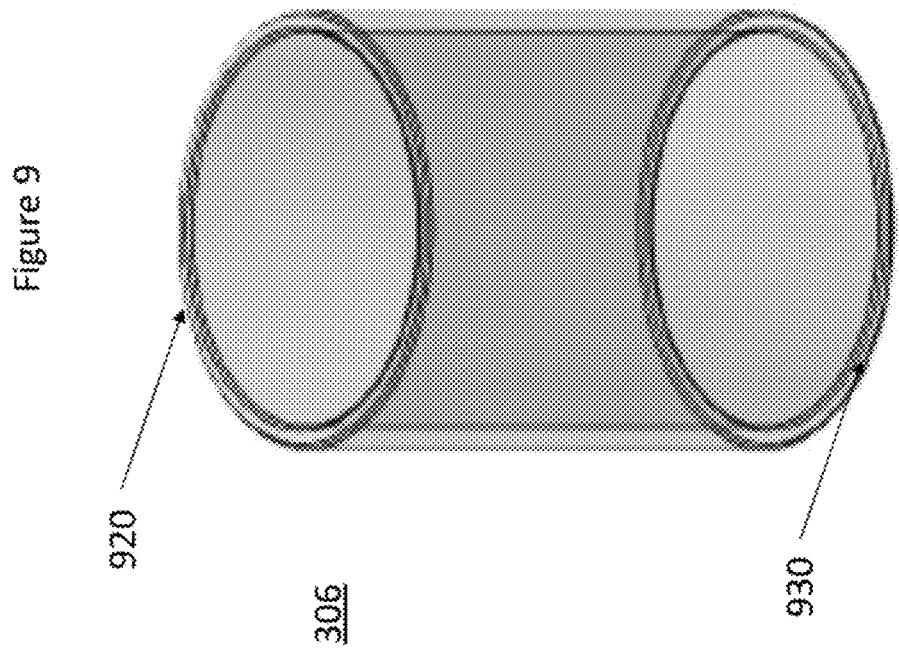
FIG. 9 depicts a housing in accordance with the present invention.

Referring to FIG. 9, chamber (306) may be a tubular cylinder of uniform diameter, extending from a first end (920) to a second end (930). Chamber (306) may, for example, have a diameter of 1 cm and a length of 1.28 cm. Chamber (306) may be made from any material that may be capable of containing the vaporizing liquid, such as polycarbonate, but may be preferably made from glass. The transparency of chamber (306) may range from completely opaque to completely clear.

Figure 8:
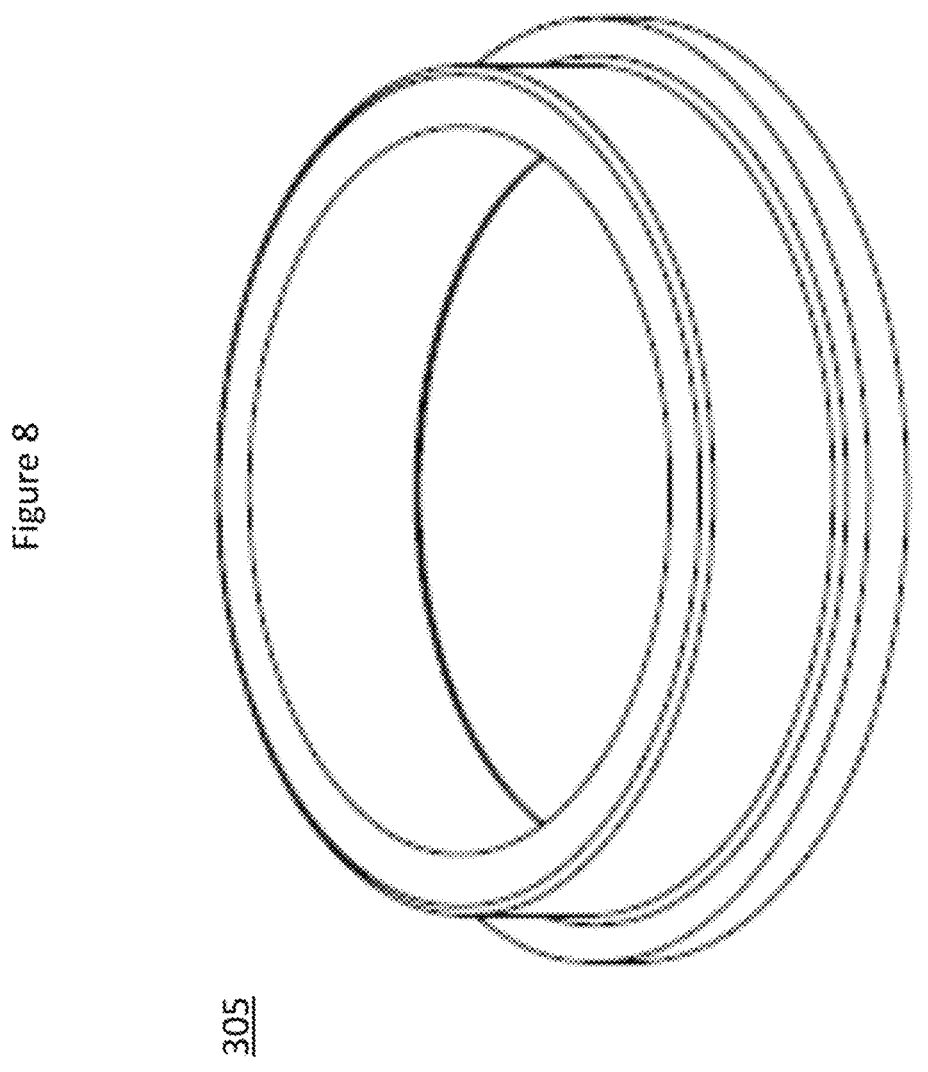
Figure 12:
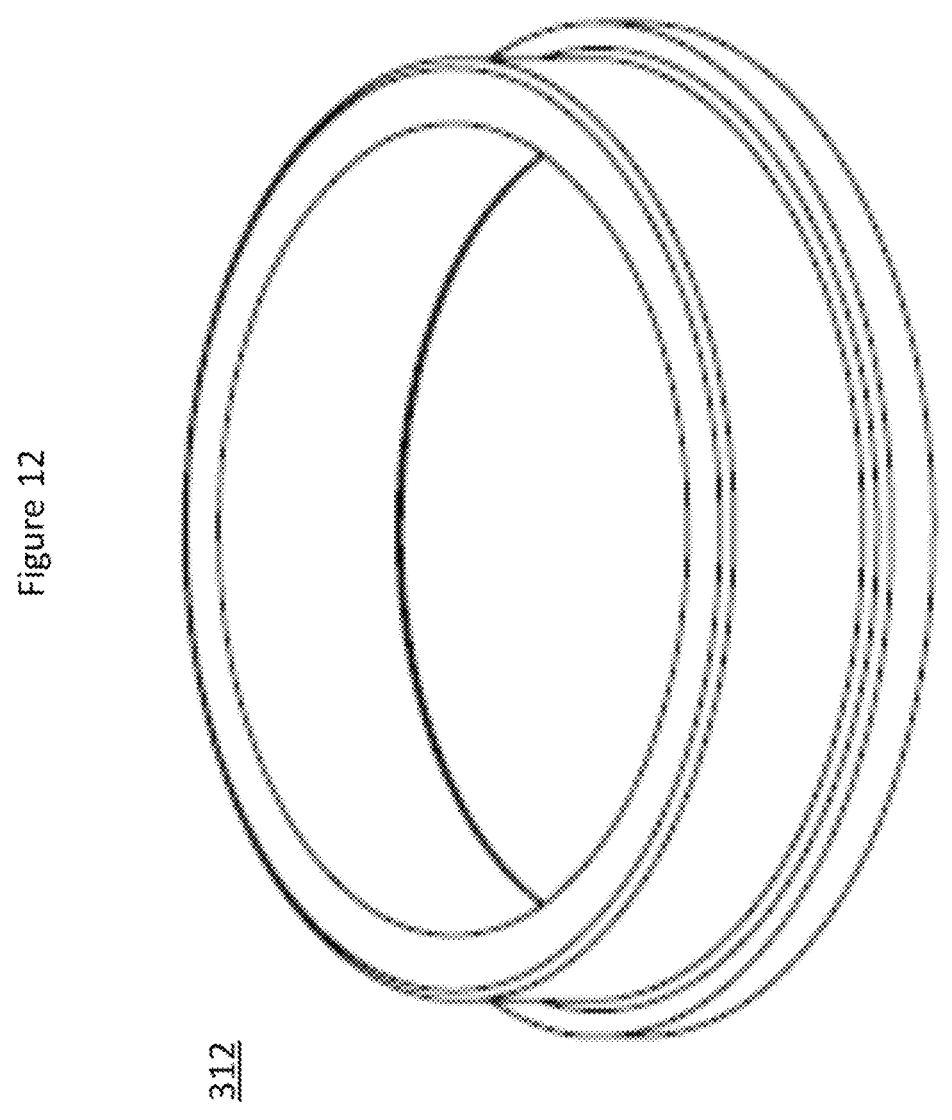

First end (920) of chamber (306) may be inserted into top adapter mounting cavity (1104). A top chamber gasket (312) may be inserted between first end (920) of chamber (306) and top adapter mounting flange (1102) to create an air-tight and/or water-tight seal between chamber (306) top adapter mounting flange (1102). Second end (930) of chamber (306) may be inserted into distal base ring cavity (703). A bottom gasket (305) may be inserted between the second end (930) of chamber (306) and distal base ring cavity (703) to create an air-tight and/or water-tight seal between chamber (306) and distal base ring cavity (703). Top gasket (312) and bottom gasket (305) may be made from, for example, rubber. Referring to FIGS. 8 and 12, top gasket (312) and bottom gasket (305) may be ring shaped. As shown in FIG. 12, top gasket (312) may be a flanged cylinder.

Figures 5A, 5B:
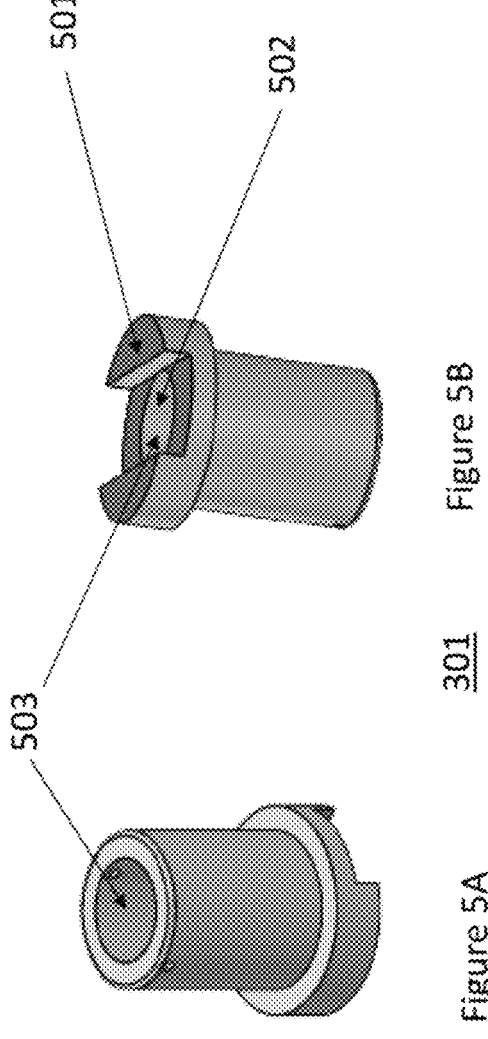
FIGS. 5A and 5B depict a distal contact connect or in accordance with the present invention.

Distal contact (301) may be inserted in inner tubular distal base cylinder (701) of distal base (303). As shown in FIG. 5, distal contact (301) may be a flanged hollow cylinder. A first end of distal contact (301) may be a tubular cylinder of a first external diameter—preferably 0.3 cm. The proximal end of the distal contact (301) may be a tubular cylinder for a certain length—preferably 0.3 cm. At the distal end of the distal contact (301), a distal flange (501) may be placed on the distal end of the tubular cylinder after the length of the tubular cylinder. The distal flange (501) may have a second distal contact connector diameter—preferably 0.4 cm—that may be larger than the first distal contact diameter at the distal end of the distal contact (301). The distal flange (501) also may have an aperture (502) that, together with the tubular cylinder of the proximal end of the distal contact connector (301) produces a distal contact connector cavity (503). The distal flange (501) also may have a distal flange thickness. The distal flange (501) may also have a notch—having a notch width—that runs across the longitudinal axis of the distal contact connector (301). Where the notch may be present, the thickness of the distal flange (501) may be decreased—preferably by 50%. The distal contact (301) can be made of any material, but may be preferably made from polished silver.

Figures 6A, 6B:
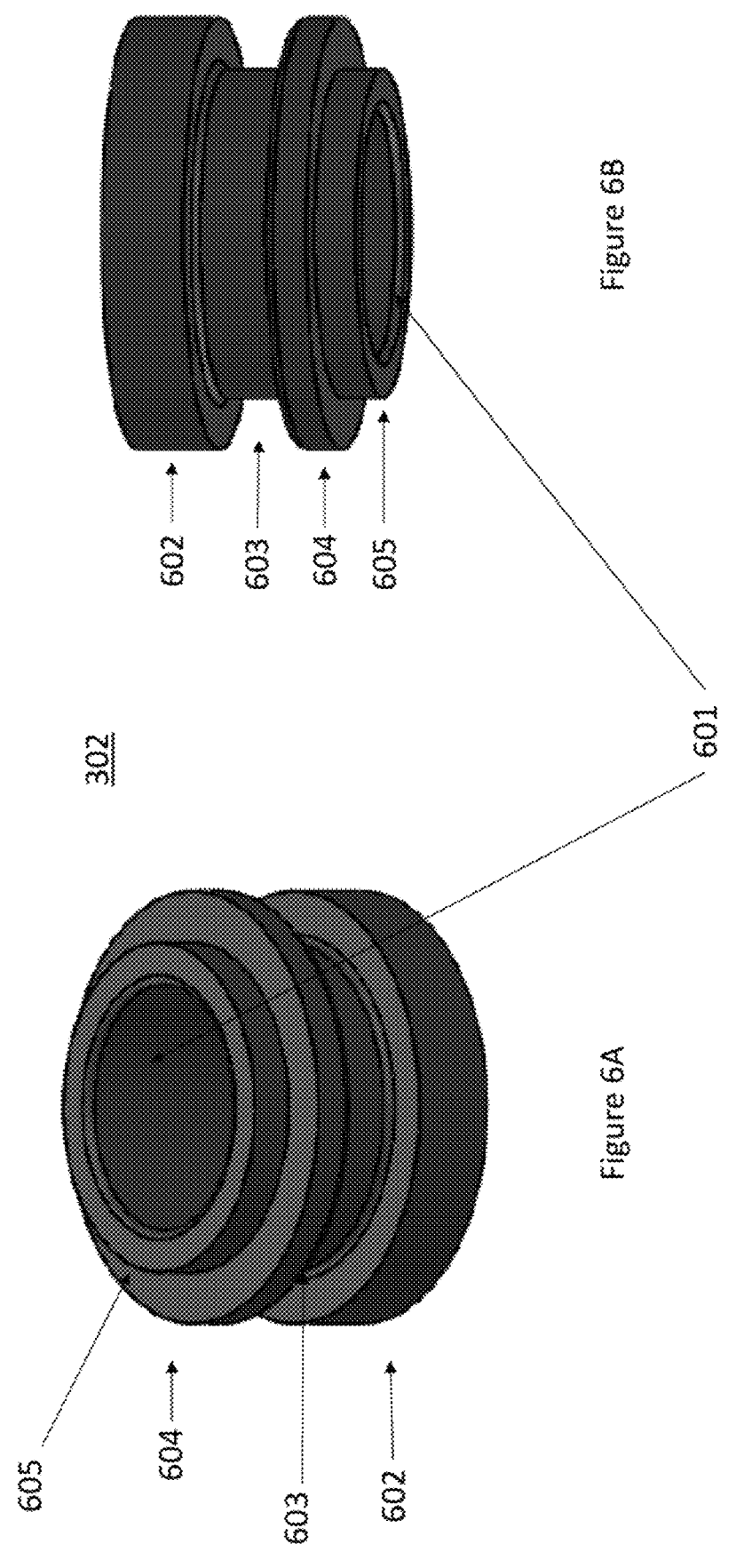
FIGS. 6A and 6B depict a distal contact gasket in accordance with the present invention.

Distal contact (301) may be made of conductive material and may be the means by which power may be initially delivered to the cartridge (300) from either the battery contact of the power source (201) or the electrical contact of a preceding cartridge. A distal contact gasket (302) may surround the distal tubular portion of distal contact (301) and may be placed between the distal contact (301) and distal base (303). Referring to FIG. 6, distal contact gasket (302) may be made from any material suitable for a gasket but may be preferably silicone rubber. Distal contact gasket (302) may comprise four successive tubular sections that are fabricated together. Each tubular section of the distal contact gasket (302) may have a distal contact gasket cavity (601) having an internal diameter that may be similar to an external diameter of the proximal portion of the distal contact connector (301)—preferably 0.3 cm. The distal tubular section (602) of the distal contact gasket (301) may have a first thickness. Preferably, the first thickness may be 0.1 cm. The distal tubular section (602) may have a first length measured axially from the distal end of the distal contact gasket toward the proximal end distal tubular section (602). This first length can preferably be 0.1 cm.

The second tubular section (603) of distal contact gasket (302) may be the next tubular section in the distal contact gasket in the proximal direction after the distal tubular section (602). The second tubular section (603) of the distal contact gasket (302) may have a second thickness that may be narrower than the first thickness of the distal tubular section (602). Preferably, this second thickness may be 0.05 cm. The second tubular section may have a second length measured axially from the proximal end of the distal tubular section to the proximal end of the second tubular section (603). This second length can preferably be 0.08 cm.

The third tubular section (604) of distal contact gasket (302) may be the next tubular section in the distal contact gasket in the proximal direction after the second tubular section (603) discussed above. The third tubular section (604) of the distal contact gasket (302) may have a third thickness that may be wider than the second thickness of the second tubular section (603). Preferably, this third thickness can be the same as the first thickness: 0.1 cm. The third tubular section (604) may have a third length measured axially from the proximal end of the second tubular section to the proximal end of the third tubular section (604). This third length can preferably be 0.04 cm.

The proximal tubular section (605) of distal contact gasket (302) may be the final tubular section in the distal contact gasket in the proximal direction after the third tubular section (604). The proximal tubular section (605) of the distal contact gasket (302) may have a fourth thickness that may be narrower than the third thickness of the third tubular section (604). Preferably, this fourth thickness can be the same as the second thickness: 0.05 cm. The proximal tubular section may have a fourth length measured axially from the proximal end of the third tubular section (604) to the proximal end of the distal contact gasket (302). This fourth length can preferably be 0.05 cm.

Figure 10:
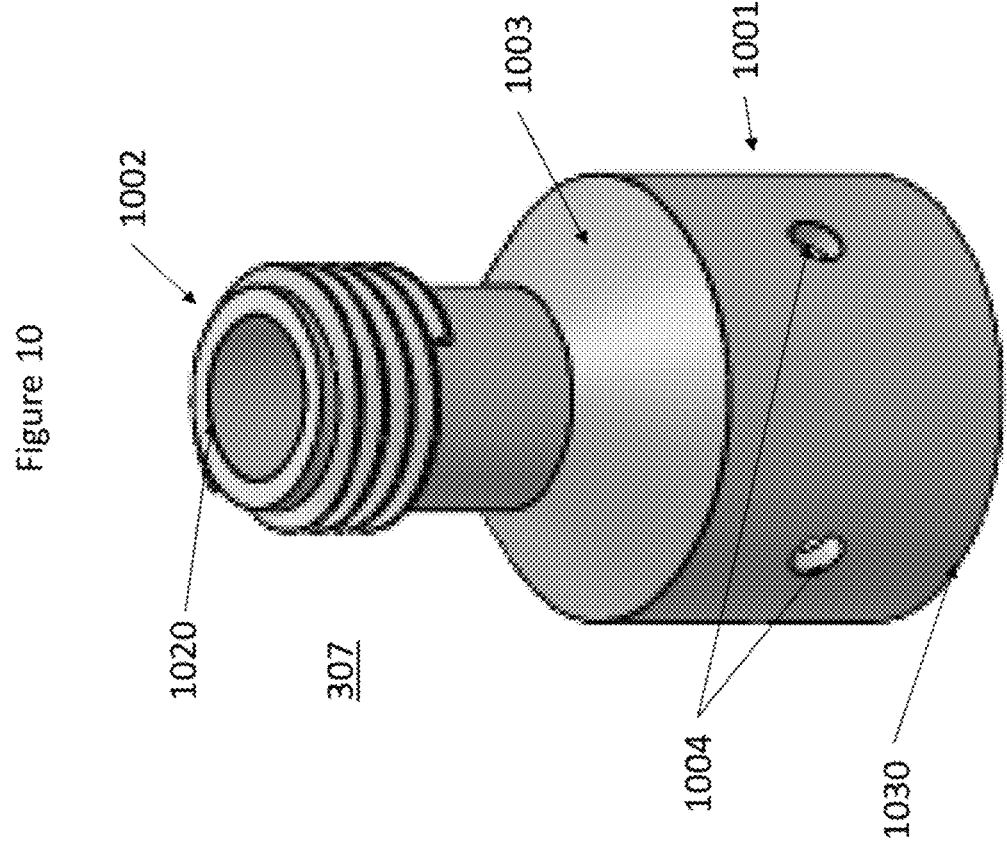
FIG. 10 depicts a cartridge chimney in accordance with the present invention.

Cartridge chimney (307) may be located within chamber (306). In its unused state, the vaporizing liquid in the cartridge would reside between the cartridge chimney (307) and the chamber (306). As shown in FIG. 10, the cartridge chimney (307) extends from a proximal end (1020) to a distal end (1030) and comprises three sections-α distal chimney tubular cylinder (1001) at the distal end of the cartridge chimney (307), a narrower proximal chimney tubular cylinder (1002) at the proximal end of the cartridge chimney (307), and a cartridge chimney nozzle transition (1003) between the distal chimney tubular cylinder (1001) and the proximal chimney tubular cylinder (1002). The cartridge chimney nozzle transition (1003) transitions the diameter of the wider distal chimney tubular cylinder (1001) to the narrower proximal chimney tubular cylinder (1002). The outer diameter of the distal chimney tubular cylinder (1001) may be preferably 0.8 cm and the preferred length of the distal chimney tubular cylinder (1001) may be preferably 0.6 cm. In contrast, the proximal chimney tubular cylinder (1002) may have a preferred diameter of 0.4 cm and a preferred length of 0.55 cm. In addition, the external surface of the proximal chimney tubular cylinder (1002) may be partially or fully threaded so that it may be operatively connected with top adapter (310). The distal chimney tubular cylinder (1001) also may have a plurality of chimney apertures (1004). The cartridge chimney (307) may be made of any material, but may be preferably made from stainless steel.

Distally internally threaded tubular cylinder (1101) may have a diameter that may be sufficient to be fitted to the top of the proximal chimney tubular cylinder (1002) of the cartridge chimney (307). Preferably, the distally internally threaded tubular cylinder (1101) may have an internal diameter of 0.4 cm, and, preferably, the externally threaded proximal chimney tubular cylinder (1002) engages the internal threads of the distally internally threaded tubular cylinder (1101) to be fit together.

While the cartridge chimney (307) and the top adapter (310) can be coupled via threads, other methods of coupling may also be envisioned such as welding, soldering, and gluing-all with or without the assistance of threads. The distally threaded tubular cylinder (1101) may have a length that may be sufficient to properly couple and engage the proximal chimney tubular cylinder (1101)—preferably 0.34 cm. The top adapter mounting flange (1102) may surround the proximal end of the distal internally threaded tubular cylinder (1101) and may extend radially from the distal internally threaded tubular cylinder (1101) a distance—preferably 0.24 cm. At that distance, the top adapter mounting flange (1102) may have a section that moves in the distal direction a distance—preferably of about 0.25 cm. This arrangement creates a top adapter mounting cavity (1104) having a radial distance and a depth that forms a ring around the distal internally threaded tubular cylinder (1101). The proximal internally threaded tubular cylinder (1103) may be connected to the top adapter mounting flange (1102) and may have a diameter that may be wider than the diameter of the distal internally threaded tubular cylinder (1101). The proximal internally threaded tubular cylinder (1101) may have an internal diameter that may be sufficient to allow the inner tubular distal base cylinder (701) of a secondary cartridge (207) to be screwed into place—preferably 0.7 cm. Alternatively, if the cartridge (300) is used as the final secondary cartridge (207), the proximal internally threaded tubular cylinder (1103) may be used to connect to a mouthpiece (208). The exterior of the top adapter (310) may contain ridges to provide assistance in screwing the cartridge (300) into the components of the customizable vaporizer. The top adapter (310) may be made of any material, but may be preferably made of brass.

A wick housing (315) may be located within the proximal end of the tubular portion of the distal base (303). Preferably, the wick housing (315) may be friction fitted into the proximal end of the tubular portion of the distal base (303) but other methods of fitting may be used instead, including threading, welding, soldering, and gluing.

Figures 15A, 15B:
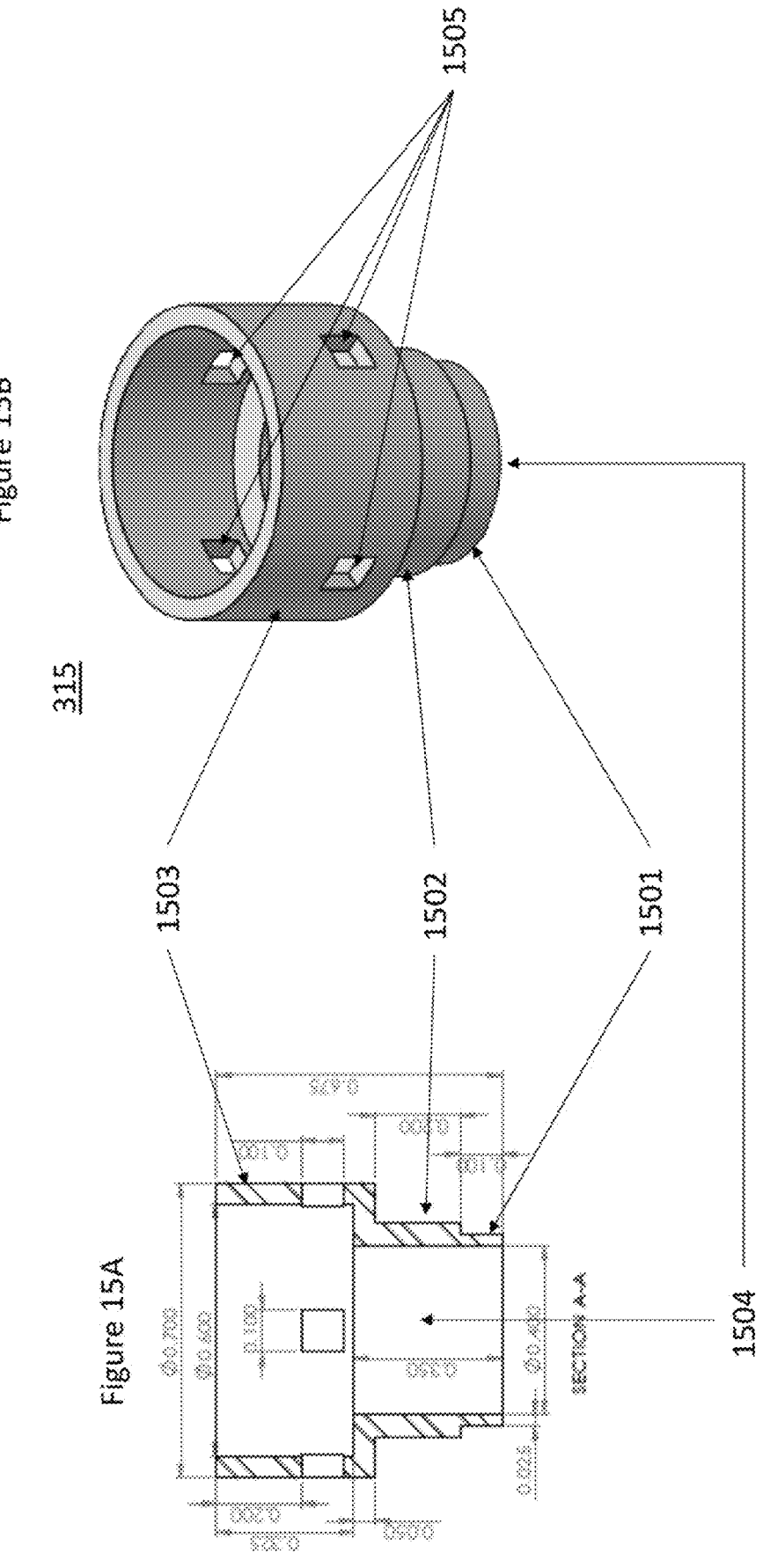
FIGS. 15A and 15B depict a wick housing in accordance with the present invention.

Referring to FIG. 15, wick housing (315) may be a single fabricated component comprising three cylinders effectively stacked on one another-α distal wick tubular cylinder (1501), a middle wick tubular cylinder (1502), and a proximal wick tubular cylinder (1503). The wick housing (315) may have a wick housing tubular cavity (1504) running longitudinally through the wick housing (315), from the distal end of the wick housing (315) to the proximal end of the wick housing (315). The distal wick tubular cylinder (1501) may have a distal wick tubular cylinder outer diameter that may be similar to the inner diameter of the tubular cavity within the distal base and a distal wick tubular cylinder height. Preferably, the distal wick tubular outer cylinder diameter may be 0.425 cm and the distal wick tubular cylinder height may be 0.1 cm.

The middle wick tubular cylinder (1502) may have a middle wick tubular cylinder diameter that may be larger than the distal wick tubular cylinder diameter. The middle wick tubular cylinder also may have a middle wick tubular cylinder height. Preferably, the middle wick tubular cylinder diameter may be 0.5 cm and the distal wick tubular cylinder height may be 0.2 cm.

The proximal wick tubular cylinder (1503) may have a proximal wick tubular cylinder diameter that may be larger than the middle wick tubular cylinder diameter and close to the diameter of the distal chimney tubular cylinder (1001) as the proximal wick tubular cylinder (1503) may be fit within the distal chimney tubular cylinder (1001). The proximal wick tubular cylinder (1503) also may have a proximal wick tubular cylinder height. Preferably, the proximal wick tubular cylinder diameter may be 0.7 cm and the proximal wick tubular cylinder height may be 0.375 cm. In addition, the proximal wick tubular cylinder may have a plurality of wick apertures (1505). As shown in FIG. 4, one or more wick apertures (1505) may be aligned with one or more chimney apertures (1004). Wick housing (315) may be made from any material, but the preferred material may be stainless steel.

A heating element (317) may be located within wick housing (315). Wick housing (315) may also contain wicking material known in the art to wick vaporizing liquid toward heating element (317). Alternatively, vaporizing liquid may be drawn to the heating element (317) due to pressure or gravity. Heating element (317) may be, for example, metal or ceramic. Heating element (317) may be a heating coil that may be constructed of a durable, electrically conductive material, such as titanium or another metal, which generates heat when subjected to an electric current. Heating element (317) may receive electricity from distal contact (301) when the portable vaporizer is operated to generate heat necessary to vaporize the fluid within the chamber (306). Heating element (317) may be connected to the distal contact (301) by having its ends pressed between the distal contact (301) and the distal contact gasket (302).

The primary cartridge (203) holds a first vaporizing liquid. This first vaporizing liquid may contain a primary ingredient—preferably an active pharmaceutical ingredient such as nicotine or a cannabinoid such as THC. The secondary cartridge (207) holds a second vaporizing liquid. This second vaporizing liquid may contain a secondary ingredient—preferably terpenes or other oils that can be vaporized to produce flavors. While, for the purposes of this discussion, only one secondary cartridge may be discussed as an example, a plurality of secondary cartridges may be attached one after another such as in FIG. 2—each having its own vaporizing liquid and providing its own effect. A mouthpiece (208) lies at the proximal end of the customizable portable vaporizer (200) after the final secondary cartridge (207).

The design of the present invention allows a single power source to drive multiple heating elements in multiple cartridges. The cartridge (300) design described herein may be used for both the primary cartridge (203) and the secondary cartridge (207).

An embodiment of the power source (201) of the customizable portable vaporizer is described, for example, in U.S. Pat. No. 10,244,792, which is incorporated herein by reference. The features of the illustrated power source (201) are typical of portable vaporizer power sources currently available on the market.

Figures 13A, 13B:
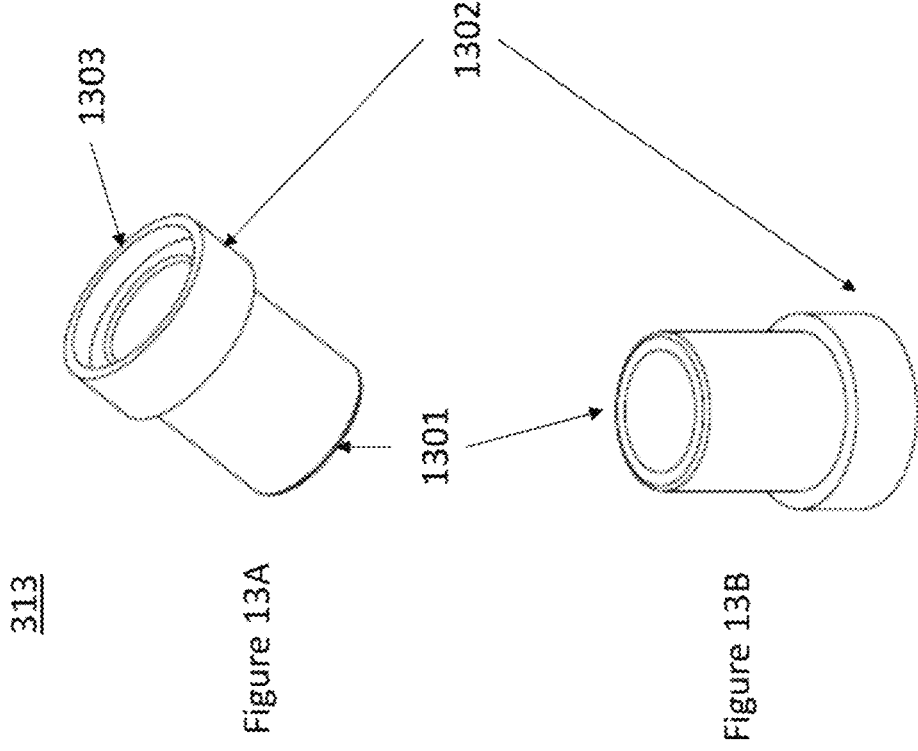
FIGS. 13A and 13B depict a chamber contact gasket in accordance with the present invention.

A chimney contact gasket (313) can be fit within the smaller proximal chimney tubular cylinder (1002). As shown in FIG. 13, the chimney contact gasket (312) may be a flanged tubular cylinder with, preferably, smooth edges, comprising a distal tubular portion (1301) and a proximal flange portion (1302). The distal tubular portion (1301) may have an outer diameter that may be preferably sufficiently small to allow for a fit within the proximal chimney tubular cylinder (1002)—preferably 0.3 cm. The distal tubular portion (1301) may have an inner diameter that may be preferably sufficiently large to allow for a fit within a chimney contact connector (314). The inner diameter of the distal tubular portion (1301) may be preferably 0.25 cm. The distal tubular portion (1301) may have a length that may be sufficiently short so that it may fit within the proximal chimney tubular cylinder (1002) until the proximal end of the proximal chimney tubular cylinder (1002) abuts the proximal flange portion (1302) of the chimney contact gasket (313). This length may be preferably 0.34 cm. The proximal flange portion (1302) of the chimney contact gasket (313) maintains a similar inner diameter as the distal tubular portion (1301) but a thicker outer diameter-preferably an outer diameter of 0.4 cm. The proximal flange portion (1302) may also optionally have a lip (1303) that extends proximally along the edge of the circumference of the proximal flange portion (1302) to ensure a proper fit with the chimney contact connector (314) inserted into the chimney contact gasket (313). The chimney contact gasket (313) may be made of any material capable of creating a seal but may be preferably made from silicone rubber.

Figures 14A, 14B:
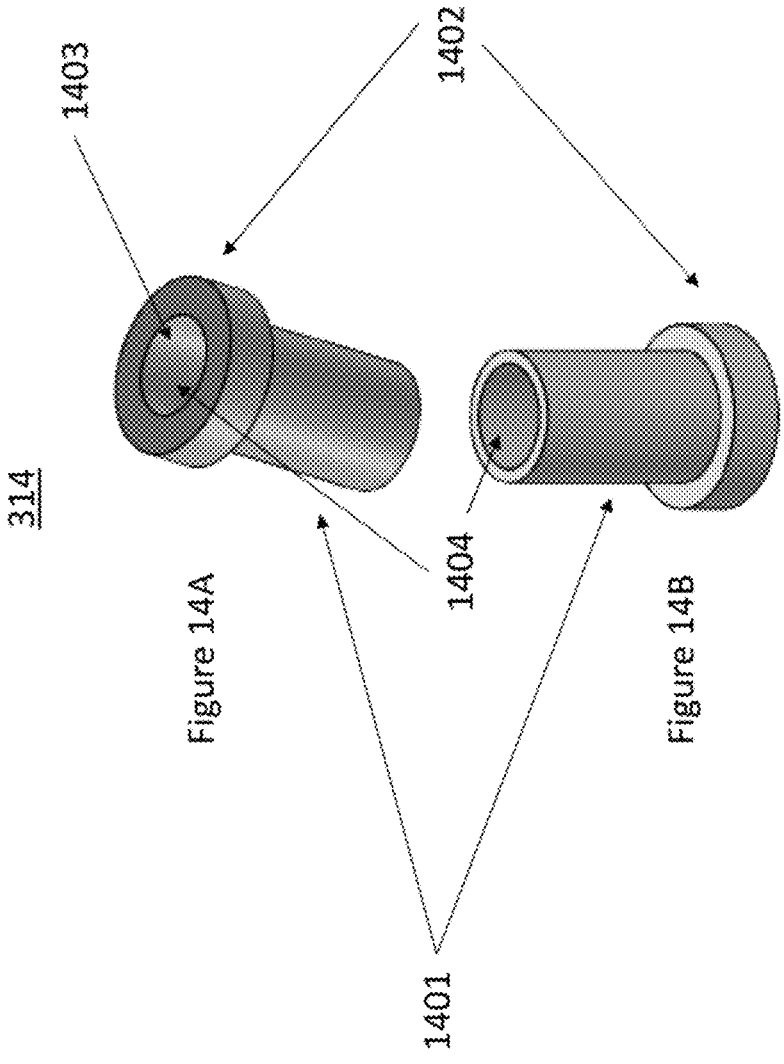
FIGS. 14A and 14B depict a chimney contact connector in accordance with the present invention.

The chimney contact connector (314) can then be fit within the chimney contact gasket (313). The chimney contact connector can be made of any conductive material and may be the means by which power may be initially delivered from the cartridge (300) to a secondary cartridge (207) or to a grounding circuit within the mouthpiece (208) to complete the circuit. The chimney contact connector (314) may be a flanged hollow cylinder as set forth in FIGS. 14A and 14B. The distal end of the chimney contact connector (314) may be a distal tubular cylinder (1401) having a first distal chimney contact diameter—preferably 0.3 cm. The distal tubular cylinder (1401) may have a certain length—preferably 0.4 cm. This length of the distal tubular cylinder (1401) may be inserted into chimney contact gasket (313). At the proximal end of the chimney contact connector (314), a proximal flange (1402) may be placed on the proximal end of the tubular cylinder after the length of the tubular cylinder. The proximal flange (1402) may have a second chimney contact connector diameter—preferably 0.4 cm—that may be larger than the first distal chimney contact diameter. The proximal flange (1402) also may have an aperture (1403) that, together with the tubular cylinder of the distal end of the chimney contact connector (314) produces a chimney contact connector cavity (1504). The chimney contact connector (314) can be made of any conductive material, but may be preferably made from polished silver.

In one embodiment, the electrical controller in the power source (201) may control the voltage across heating element (317) to control the temperature of the heating element (317) as is known in the art. As is known in the art, for a given material for a heating element (317), it is known that a certain voltage will yield a certain temperature. In one embodiment, the customizable vaporizer contains a controller that will allow the user to customizer the temperature at which it will heat the vaporizing fluid in a particular cartridge (300). This may have significant therapeutic benefits because each active ingredient may have an optimal vaporization temperature.

An insulated wire (318) may electrically connect (directly or indirectly) the distal contact (301) and the chimney contact connector (314). The insulated wire (318) may be made from any conductive material but may be preferably made from polished silver. The insulation for the insulated wire (318) may be preferably made from a non-conductive material suitable for wire insulation known in the art that can also protect the conductive portion of the insulated wire (318) from fouling within the cartridge chimney (307) and wick housing (315). The insulated wire (318) may directly connect the heating element (317) with the chimney contact connector (314) as set forth in FIG. 4. The electrical connections for the insulated wire (318) may be made via any method known in the art (soldering, welding, press-fitting, twisting, etc.). The insulated wire (318) may be preferably connected to chimney contact connector (314) by being press fitting the conductive portion of the insulated wire (318) between the chimney contact connector (314) and the chimney contact gasket (313). The insulated wire (318) may be preferable connected to the heating element (317) by soldering the conductive portion of the insulated wire (318) to the heating element (317).

The electrical circuit arrangement set forth in FIG. 4 places the distal contact connector (301), heating element (317), and chimney contact connector (314) in an electrical series. An alternative would be to connect these components in parallel. To do so, heating element (317) may remain in direct electrical connection with the distal contact connector (301). The insulated wire (318) might then directly connect the distal contact (301) and the chimney contact connector (314). In this parallel arrangement, the insulated wire (318) may be press-fit between the distal contact gasket (302) and the distal contact connector (301).

Figure 16:
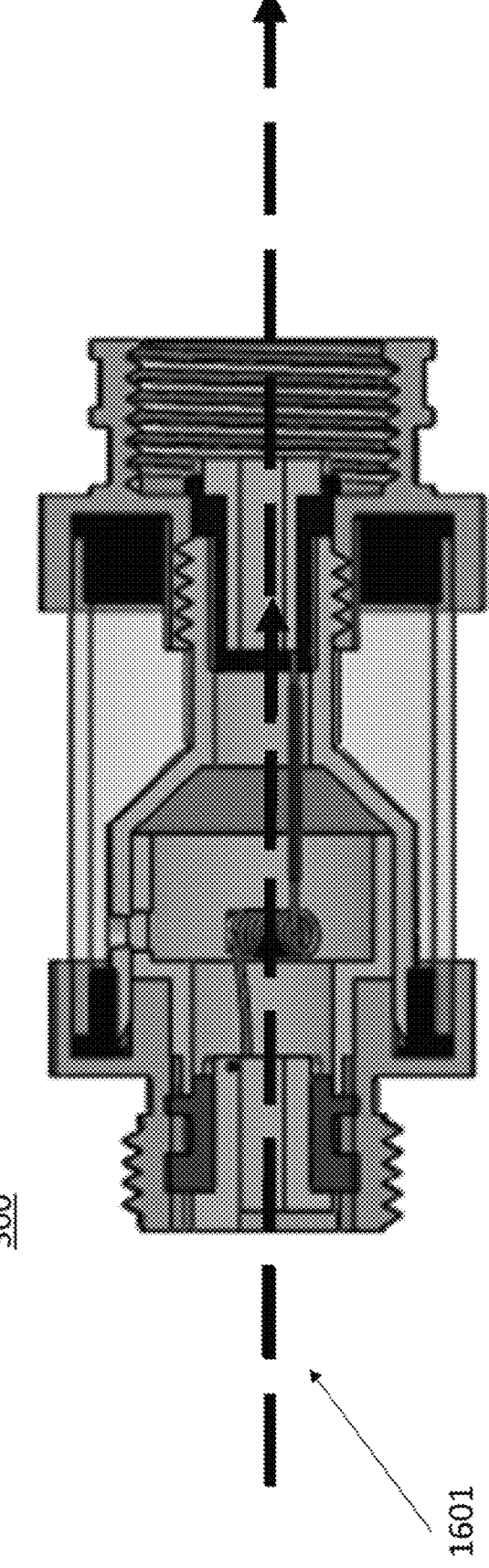
FIG. 16 depicts a cross-sectional view of the cartridge depicted in FIG. 3.

The reservoir (311) may be filled with a vaporizing liquid and sealed. If it is a primary cartridge (203), the reservoir (311) may contain a vaporizing liquid containing an active ingredient such as nicotine or THC. If it is a secondary cartridge (207), the cartridge may contain a vaporizing liquid containing terpenes or flavors. The cartridge (300), from distal to proximal end, may have a clear airflow path (1601) down the longitudinal axis of the cartridge as set forth in FIG. 16. This is because each component described above may have a tubular section that will allow air coming from the air apertures (202) of the customizable portable vaporizer (200). The mouthpiece (208) is the ultimate vapor exhaust.

The mouthpiece (208) may be any mouthpiece known in the art for use with portable vaporizers. The mouthpiece (208) comprises a mouthpiece tube, which in some embodiments can be substantially transparent, that may be received into a proximal cavity into of a mouthpiece base. A distal portion of the mouthpiece base comprises an O-ring seat that receives an O-ring. A mouthpiece mount may have an externally threaded passage that can be used to engage the proximal portion of the top adapter (310) so that the mouthpiece module can be tightened atop the cartridge.

In use, the user inserts the mouthpiece (208) into the user's mouth, presses the battery button, and draws a breath. Pressing the button activates the power source (201). Alternatively, the customizable vaporizer may also be powered automatically upon by a pressure sensor indicting that a user may be drawing in a breath thereby creating negative pressure, which can actuate a the electronic controller to start operation. Via the power source, electricity travels through the distal contact (301) to the heating element (317) and the chimney contact connector (314). If another cartridge (300) is connected at the proximal end via the top adapter (310), the electricity will travel through the chimney contact connector (314) to the other cartridge's distal contact connector (301). Via the other cartridge's distal contact connector (301), the electricity will move to that cartridge's heating element (317). In this fashion, two heating elements can be powered using a single power source (201).

In the primary cartridge (203), while a user is inhaling through the mouthpiece (208), the wick housing (315) draws in the vaporizing liquid into contact with the heating element (317). The heating element heats the vaporizing fluid to the vaporization temperature. The active ingredient within the vaporizing liquid may turn into a vapor and travels through the airflow (1601) up the cartridge chimney (307), through the chimney contact connector (317), and out the top adapter (310). The vapors may leave the chimney contact connector (317) and enter the secondary cartridge (207).

In any secondary cartridges (i.e. 207), the vapors from the preceding cartridge (which could be the primary cartridge (203)) may travel through the distal contact connector (301), up through the heating element (317) as that heating element may be also vaporizing the vaporizing liquid in the secondary cartridge (207). The active ingredient(s) of the vaporizing liquid in the secondary cartridge (207) are then vaporized as well in the same manner as the active ingredient(s) of the vaporizing liquid of the preceding cartridge (including the primary cartridge (203)). Vapors of the active ingredients from the primary cartridge (203) and the secondary cartridge (207) reside together in the cartridge chimney (307). They then flow up through the chimney contact connector (317), out the top adapter (310), into the mouthpiece (208), and into the user's mouth. As such, the user gets the benefits of all vapors formed in the cartridges.

While the invention has been described in detail with reference to embodiments for the purposes of making a complete disclosure of the invention, such embodiments are merely exemplary and are not intended to be limiting or represent an exhaustive enumeration of all aspects of the invention. It will be apparent to those of ordinary skill in the art that numerous changes may be made in such details, and the invention is capable of being embodied in other forms, without departing from the spirit, essential characteristics, and principles of the invention. Also, the benefits, advantages, solutions to problems, and any elements that may allow or facilitate any benefit, advantage, or solution are not to be construed as critical, required, or essential to the invention. The scope of the invention is to be limited only by the appended claims.

What is claimed is:

1. A vaporizer cartridge comprising:
a housing extending from a first end to a second end;
a heating element contained within the housing;
a distal contact located at a first end of the vaporizer cartridge; and
a chimney contact connector located at a second end of the vaporizer cartridge; wherein the distal contact is electrically connected to the heating element;
wherein the heating element is electrically connected to the chimney contact connector; and
wherein the chimney contact connector is configured to be electrically connected to a secondary vaporizer cartridge.

2. The vaporizer cartridge of claim 1, further comprising a chimney contained within the housing and extending from the first end of the housing to the second end of the housing.

3. The vaporizer cartridge of claim 2, wherein the heating element is electrically connected to the chimney contact connector via one or more wires.

4. The vaporizer cartridge of claim 3, wherein the one or more wires is located within the chimney.

5. The vaporizer cartridge of claim 1, further comprising an adapter at the second end of the housing, wherein the chimney contact connector is contained within the adapter.

6. The vaporizer cartridge of claim 5, further comprising a base at the first end of the housing, wherein the distal contact is contained within the base.

7. The vaporizer of claim 6, wherein the adapter is configured to be coupled with the base such that the distal contact is in electrical communication with the chimney contact connector.

8. The vaporizer cartridge of claim 5, wherein the adapter is configured to be coupled with a mouthpiece.

9. The vaporizer cartridge of claim 6, wherein the base is configured to be coupled with a power source such that the power source is in electrical communication with the distal contact.

10. The vaporizer cartridge of claim 1, wherein the heating element is a heating coil.

11. A portable vaporizer comprising:
a power source,
a mouthpiece, and
a vaporizer cartridge coupled to the power source and the mouthpiece, the first-vaporizer cartridge comprising:
a housing extending from a first end to a second end;
a heating element contained within the housing;
a distal contact located at a first end of the vaporizer cartridge; and a chimney contact connector located at a second end of the vaporizer cartridge; wherein the distal contact is electrically connected to the heating element;

wherein the heating element is electrically connected to the chimney contact connector; and wherein the chimney contact connector is configured to be electrically connected to a secondary vapor cartridge.

12. The portable vaporizer of claim 11, wherein the vaporizer cartridge further comprises a chimney contained within the housing and extending from the first end of the housing to the second end of the housing.

13. The portable vaporizer of claim 12, wherein the heating element is electrically connected to the chimney contact connector via one or more wires.

14. The portable vaporizer of claim 13, wherein the one or more wires is located within the chimney.

15. The portable vaporizer of claim 11, wherein the vaporizer cartridge further comprises an adapter at the second end of the housing, wherein the chimney contact connector is contained within the adapter.

16. The portable vaporizer of claim 15, wherein the vaporizer cartridge further comprises a base at the first end of the housing, wherein the distal contact is contained within the base.

17. The portable vaporizer of claim 16, wherein the adapter is configured to be coupled with the base such that the distal contact is in electrical communication with the chimney contact connector.

18. The portable vaporizer of claim 15, wherein the adapter is configured to be coupled with a mouthpiece.

19. The portable vaporizer of claim 16, wherein the base is configured to be coupled with a power source such that the power source is in electrical communication with the distal contact.

20. The portable vaporizer of claim 11, wherein the heating element is a heating coil.

* * * * *